(12) United States Patent
Krempl et al.

(10) Patent No.: US 6,972,841 B2
(45) Date of Patent: Dec. 6, 2005

(54) METHOD AND APPARATUS FOR DETERMINING THE NON-VOLATILE COMPONENT OF AEROSOL PARTICLES IN A GAS SAMPLE

(75) Inventors: Peter W. Krempl, Kainbach bei Graz (AT); Christian Reiter, Graz (AT); Wolfgang Schindler, Graz (AT); Wolfgang Singer, Eisbach/Rein (AT)

(73) Assignee: AVL List GmbH, Graz (AT)

( * ) Notice: Subject to any disclaimer, the term of this patent is extended or adjusted under 35 U.S.C. 154(b) by 293 days.

(21) Appl. No.: 10/302,980

(22) Filed: Nov. 25, 2002

(65) Prior Publication Data

US 2003/0123059 A1  Jul. 3, 2003

(30) Foreign Application Priority Data

Nov. 26, 2001  (AT) .............................. A 1849/2001

(51) Int. Cl.⁷ ............................................. G01N 15/02
(52) U.S. Cl. ....................................................... 356/338
(58) Field of Search .... 356/335–343; 73/23.21–23.28, 73/28.01–28.06, 433, 434, 1.06, 1.34, 1.31, 73/32 R

(56) References Cited

U.S. PATENT DOCUMENTS

| | | | |
|---|---|---|---|
| 3,561,253 A | | 2/1971 | Dorman |
| 5,892,141 A | | 4/1999 | Jones et al. |
| 6,181,419 B1 | | 1/2001 | Snelling et al. |
| 6,295,861 B1 | * | 10/2001 | Tom et al. ................. 73/24.06 |
| 6,502,450 B1 | * | 1/2003 | Patashnick et al. ........ 73/23.21 |

FOREIGN PATENT DOCUMENTS

| | | |
|---|---|---|
| DE | 268530 | 5/1989 |
| DE | 10061976 | 6/2001 |
| WO | 8802480 | 4/1988 |

* cited by examiner

*Primary Examiner*—Tu T. Nguyen
(74) *Attorney, Agent, or Firm*—Dykema Gossett PLLC

(57) ABSTRACT

The invention relates to a method for determining the non-volatile component of aerosol particles in a gas sample, especially in the exhaust gas of internal combustion engines, where the aerosol particles are deposited on an oscillating sensor (2) of at least one crystal microbalance (3), and the change in at least one oscillation parameter of the oscillating sensor is employed as measurement variable. According to the invention the oscillating sensor (2) of at least one crystal microbalance (3) is maintained at a temperature of more than 200° C. during deposition of the aerosol particles, and preferably between 250° C. and 350° C.

22 Claims, 1 Drawing Sheet

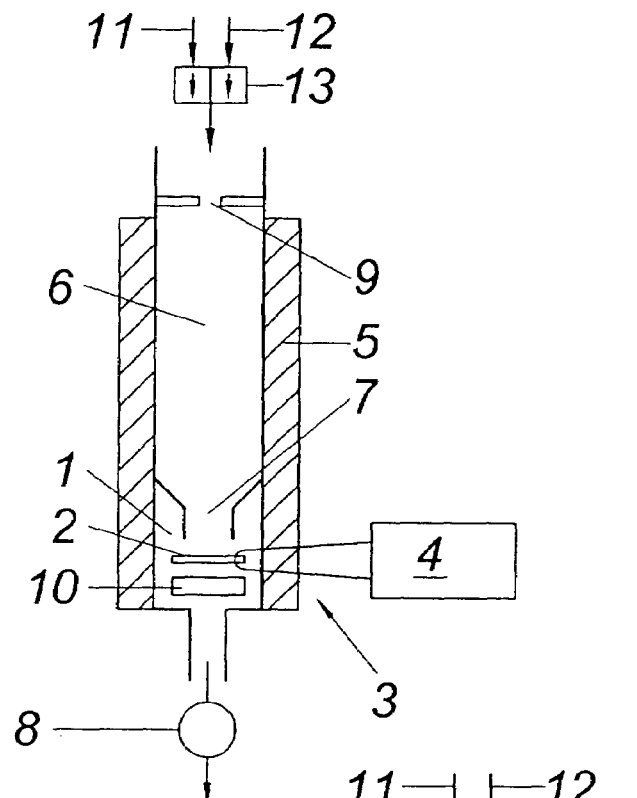
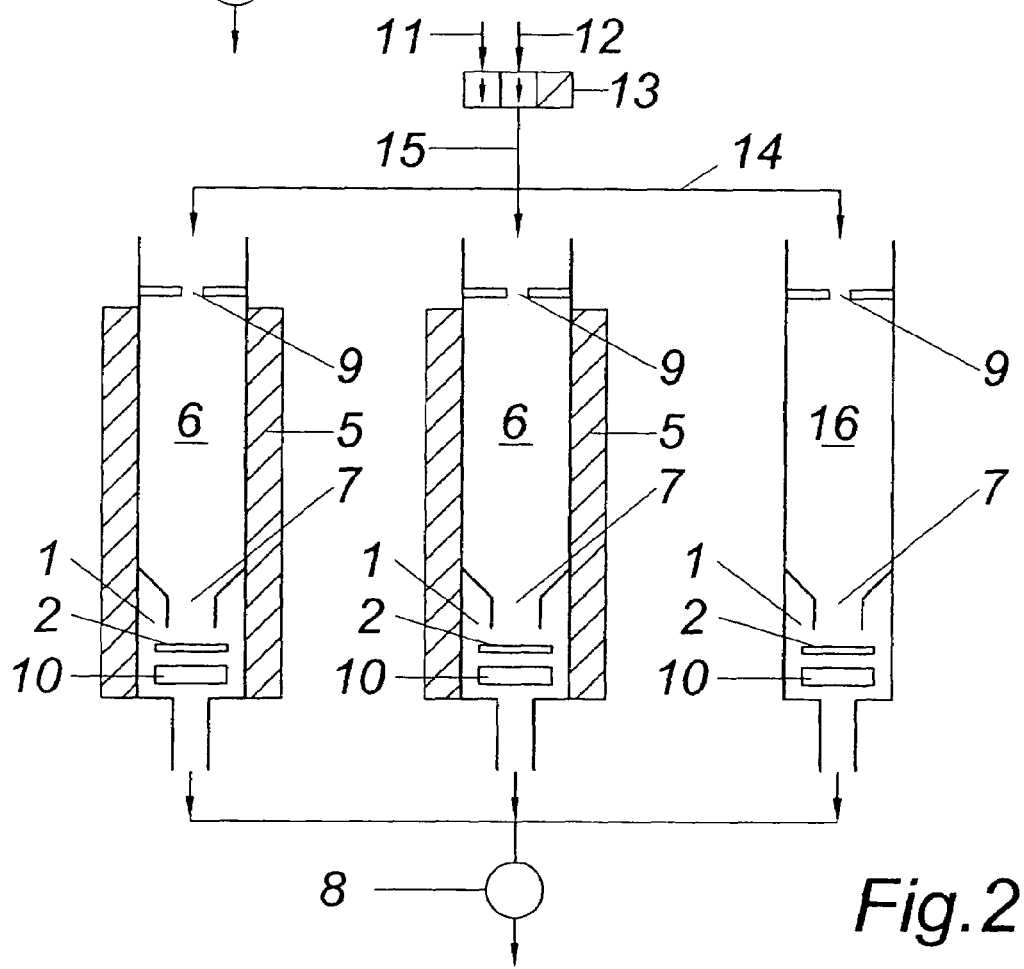
Fig.1
Fig.2

METHOD AND APPARATUS FOR DETERMINING THE NON-VOLATILE COMPONENT OF AEROSOL PARTICLES IN A GAS SAMPLE

BACKGROUND OF THE INVENTION

This invention relates to a method and apparatus for determining the non-volatile component of aerosol particles in a gas sample, particularly in the exhaust gas of internal combustion engines, where the aerosol particles are deposited on an oscillating sensor of at least one crystal microbalance, and the change in at least one oscillation parameter of the oscillating sensor is employed as measurement variable.

DESCRIPTION OF THE PRIOR ART

Important variables for assessment of the emissions of internal combustion engines include particle mass and chemical composition of the particles. An interesting fraction is represented by the content of graphitic particles (soot), since these are assumed to be health-relevant. It is usually determined by the smoke-value method or by loading filters with emission particles and subjecting them to chemical analysis.

The smoke-value method is based on the change in optical reflectance behavior of the filter due to particle load. A decrease in reflectance is mainly due to the carbon content of the particles. The quantity of interest, i.e., the soot concentration in the exhaust gas, is determined by calibration. The method suffers from the disadvantage that the mass required for computing the concentration cannot be directly measured.

Chemical analysis of the filter load is effected by extraction of the particle-loaded filter using an organic solvent. The fraction which is not organically soluble will remain on the filter. By measuring the mass of the filter without load, and that of the filter with load, and that of the extracted filter, the total mass of particles and the contributions of the soluble and non-soluble fractions may be determined. This method has the disadvantage that the analyses are time-consuming and require a laboratory of high standard.

Increasingly restrictive emission regulations demand a continuous reduction of particle mass concentrations in the exhaust gas. If these concentrations are very low the measuring methods described above will result in very long measurement times. Due to the integrative measurement principle particle emission may be determined only over the total time of measurement, so that the temporal resolution to be achieved by these methods will be rather low.

The use of gravimetric techniques employing a crystal microbalance for analysis of aerosol particles is standard knowledge. A method and device of this type is described in U.S. Pat. No. 3,561,253 A. The device comprises a measuring cell with a vacuum pump connected to the outlet, into which the aerosol to be analyzed is introduced via a nozzle and deposited directly on the sensitive surface of an oscillator quartz. Precipitation of the particles from the aerosol is effected in the individual embodiments by impaction and/or by electrostatic precipitation. The particles deposited on the oscillator quartz change the resonance frequency of the crystal, and this shift in resonance frequency is used as a measure for the particle concentration in the carrier gas. With this method only the total concentration of all particles in the carrier gas can be determined, whilst it will not be possible to determine the non-volatile component of particles, as for instance in the exhaust gas of internal combustion engines.

DE 100 61 976 A1 describes a device for quantitative and qualitative analysis of particles in gases, where an oscillating sensor which is fixed relative to the measuring cell, and an orifice plate which moves relative to the sensor surface are used for particle deposition, in order to achieve a maximum range of measurement with a linear characteristic.

Another application of a crystal microbalance for determining particle mass concentrations in aerosols is disclosed in U.S. Pat. No. 5,892,141 A. Loading the particles onto the micro-balance is achieved by electrostatic precipitation. In contrast to U.S. Pat. No. 3,561,253 A cited above, measurement here is performed only after the particles have been deposited. The oscillating sensor is then heated by means of a laser beam and an oxidizing atmosphere is introduced into the measuring cell. This will cause the particles to be reduced pyrolytically; the change in resonance frequency resulting therefrom will then be measured. The particles deposited on the sensor are at least partly removed, which permits the determination of individual particle fractions or their volatile parts. Due to the phase of particle deposition preceding the measurement, which takes a certain period of time, a summation effect occurs which prohibits measuring of the particle concentration with high temporal resolution. On-line determination of soot concentration is thus not possible.

WO 88/02480 A1 describes a device for the analysis of depositions on an oscillating sensor, where after deposition of the substance to be measured a number of different temperature levels are established and the composition of the substance is analysed thermo-gravimetrically. This method is of the same type as that cited above in U.S. Pat. No. 5,892,141 A showing the disadvantages already mentioned. Specifically, no online-determination of the soot content will be possible.

U.S. Pat. No. 6,181,419 A discloses a novel method for determining the volume of soot in exhaust gas. By means of a high-energy laser pulse the soot particles are induced to glow, and the intensity and development over time of the light emitted by the glowing particles are utilized to determine volume concentration.

From DD 268 530 A1 a method and device are known for determination of the concentration of mercury in gases, using a metallic contact zone which specifically adsorbs mercury and on which mercury is bound in the form of amalgam. An acoustic surface wave propagates through the metallic contact zone, its propagation velocity changing with the amalgam content of the zone. The temperature of the crystal may be raised above 100° C. in order to suppress condensation of water vapor. The contact zone is thermally regenerated, the time during which heat is applied being controlled by the frequency of oscillation.

Due to the specifically chosen contact zone the method responds exclusively to the volatile mercury fractions of the gas. Other volatile compounds or non-volatile components of aerosol particles in a gas sample cannot be determined by this method.

SUMMARY OF THE INVENTION

It is the object of the present invention to gravimetrically determine the concentration of non-volatile components of aerosol particles in a gas sample, specifically the soot concentration in the exhaust gas of internal combustion engines, and to achieve high temporal resolution and high mass sensitivity of the measurements.

This object is achieved by keeping the oscillating sensor of at least one crystal microbalance during the deposition period of the aerosol particles at a temperature of more than 200° C., preferably between 250° C. and 350° C. It is of particular advantage to thermostabilize the gas sample at a temperature of more than 200° C., and preferably between 250° C. and 350° C., before it meets the oscillating sensor of the microbalance. Due to the elevated temperature the volatile constituents adsorbed on or in the aerosol particles are released and do not contribute to the measurement result, from which the concentration of the non-volatile component (e.g. soot particles in the exhaust gas) may thus be directly inferred.

The method is therefore particularly well suited for the measuring of emissions at low mass concentration and with high temporal resolution.

After a critical loading of the oscillating sensor has been reached the sensor is heated to more than 500° C., and preferably more than 600° C., in order to pyrolytically remove the deposited graphitic component of the aerosol particles. This heating phase, which follows the measuring phase and during which the burning temperature of the soot is attained, results in fast and simple cleaning of the sensor element, which will then be ready for further measurements.

According to the invention the change in resonance frequency of the oscillating sensor is monitored during the pyrolytic removal of the graphitic component, so that the burning process may be controlled. The oscillating sensor or the measuring cell may be subjected to an oxidizing atmosphere, for instance clean air, before or during the pyrolytic removal of the graphitic component.

In accordance with the invention the method may also use a number of microbalances whose oscillating sensors are maintained at different temperature levels. In this context the proposal is put forward that for separate measurement of the non-volatile graphitic particles and the mineral particles the temperature of the oscillating sensor of a first crystal microbalance be kept at more than 200° C., preferably between 250° C. and 350° C., while the temperature of the oscillating sensor of a second crystal microbalance be kept at more than 500° C. In order to simultaneously measure the total particle content the temperature of the oscillating sensor of a third crystal microbalance may be kept at a lower temperature.

The accuracy of the measurement results may be further improved by using at least two oscillator parameters of the oscillating sensor for determination of the measured quantity, i.e., preferably resonance frequency and attenuation, thereby compensating for a non-mass-proportional change in resonance frequency which is caused by the viscoelastic properties of the particles deposited.

Sampling can be performed by conventional techniques, and the dilution ratio must be chosen such that the desired duration of the measurement process will be achieved without exceeding the permissible mass load of the crystal microbalance.

An apparatus for determination of the non-volatile component of aerosol particles in a gas sample, in particular in the exhaust gas of an internal combustion engine, with at least one measuring cell provided with a gas inlet and containing an oscillating sensor of a crystal microbalance which is subjected to the gas sample, is characterized according to the invention by providing the oscillating sensor with a thermostat device keeping it at a temperature of more than 200° C., preferably between 250° C. and 350° C.

According to a further characteristic of the invention the thermostat device comprises a heating chamber placed before the measuring cell and including a nozzle plate for the passage of the gas into the measuring cell.

BRIEF DESCRIPTION OF THE DRAWINGS

The invention will be further described below, with reference to the enclosed drawings, wherein FIG. 1 shows an apparatus according to the invention for determining the non-volatile component of aerosol particles in a gas sample, and FIG. 2 shows a variant of the apparatus of FIG. 1 with a number of measuring cells thermostabilised at different temperatures.

DETAILED DESCRIPTION OF THE PREFERRED EMBODIMENTS

The apparatus shown in FIG. 1 comprises a measuring cell 1 containing an oscillating sensor 2 of a crystal microbalance summarily designated 3. The oscillator circuit together with circuitry controlling the oscillator and circuitry for data input, data storage, and data display of the microbalance is referred to as 4. The oscillating sensor 2 is provided with a thermostat device 5 in the form of an envelope of the measuring cell 1 and a heating chamber 6 in front of the measuring cell 1, such that temperatures of more than 200° C., preferably between 250° C. and 350° C., may be established in the measuring cell. The particles are deposited onto the sensitive surface of the oscillating sensor 2 via a nozzle plate 7 placed at the end of the heating chamber 6.

In the variant shown deposition of the particles is effected by impaction, but electrostatic precipitation might also be used. In order to be able to deposit even very small particles (of size 10–20 nm) on the oscillating sensor 2, low-pressure impaction is used. To this end the outlet of the measuring cell 1 is connected to a vacuum pump 8 and the gas inlet of the heating chamber 6 is provided with an orifice 9 which is configured as a critical nozzle. The critical nozzle stabilizes the flow through the chamber once a certain pressure difference is established at the nozzle and generates a partial vacuum of 20 to 500 mbar in the measuring cell 1. The nozzle plate 7 provided with one or more nozzle openings permits targeted deposition on the sensitive region of the oscillating sensor. Position, number and size of the nozzle openings in the nozzle plate 7, their position relative to the oscillating sensor 2 and the pressure prevailing in the measuring cell 1 determine the cut-off-diameter of the configuration. The definition of the cut-off-diameter states that particles of this diameter are deposited with a probability of 50%. Smaller or larger particles are deposited with lower or higher probability.

Separation of the volatile fraction of the aerosol occurs between the orifice 9 (i.e., the critical nozzle) and the oscillating sensor 2. In order to enable separation of the volatile fraction the exhaust gas must be heated to a temperature of at least 200° C., or preferably 300° C. This is achieved by thermostabilizing the heating chamber 6 and the adjacent measuring cell 1 between critical nozzle and nozzle plate 7 at the desired temperature.

With the exception of the particle loading phase the temperature of the oscillating sensor 2 may be measured indirectly via the temperature dependence of the resonance frequency. A piezoelectric BAW-resonator made from temperature-stable material, whose thickness shear mode is excited, is preferably chosen for the sensor element. Preferred is the use of resonators exhibiting temperature compensation at the desired operating temperature. In general, the temperature dependence of the characteristic frequency has the form of a parabola, which implies that the characteristic frequency has a maximum at a certain critical temperature. Temperature control may now act in such a way that the maximum of the characteristic frequency is attained, which will then determine the temperature of the configuration. A further advantage of this temperature compensation is that temperature fluctuations of the exhaust gas will produce only very small changes in the measuring signal so that accuracy will be improved.

A resistance- or radiation-type heating element 10 permitting temperatures of more than 500° C., and preferably more than 600° C., to be obtained, is provided for removal of the deposit on the oscillating sensor 2. By heating the deposited load to approximately 600° C. using the heating element 10, which is placed in the immediate vicinity of the resonator or deposit in the measuring cell 1, the graphitic component, i.e., the soot particles can be removed from the sensor surface.

On account of the high combustion temperature the material chosen for the oscillating sensors should be such that the crystals are thermally stable up to temperatures of more than 600° C., as for instance $GaPO_4$ or crystals of the langasite structure family (preferably LGS ($La_3Ga_5SiO_{14}$), LNG ($Ln_3Nb_{0.5}Ga_{5.5}O_{14}$) and LTG ($Ln_3Ta_{0.5}Ga_{5.5}O_{14}$) with Ln=La, Pr, Nd as well as SGG ($Sr_3Ga_2Ge_4O_{14}$) and CGG ($Ca_3Ga_2Ge_4O_{14}$)).

The piezoelectric resonator of the oscillating sensor 2 is induced to oscillate at its characteristic frequency by means of an electronic oscillator circuit 4. Output signals of the oscillator are the resonance frequency of the BAW-resonator and a signal proportional to the attenuation of the resonator. Other oscillation-relevant quantities include the voltage at the resonator, current flow through the resonator, power at the resonator, and phase, depending on the respective oscillator design. The resonance frequency whose change at low mass load is proportional to particulate mass, is employed to determine particle mass concentration resulting from the sensitivity of the sensor element to mass load, the change of resonance frequency over time, and the known flow rate.

The attenuation signal may be used to assess the acoustic properties of the deposited particle layer. If a layer is non-vitreous its viscoelastic properties will lead to a decrease in resonance frequency that is not proportional to mass. By including the attenuation signal in the signal evaluation process, the deviation from the actually present particulate mass may be compensated and/or the measurement range may be established by defining a maximum permissible attenuation.

Measuring Process

While the apparatus is heated to operating temperature clean air (arrow 11) is taken through the measuring cell 1.

For aerosol particle loading a valve 13 is switched to exhaust gas (arrow 12), the loading process is terminated by switching back to clean air. The switchover from clean air to exhaust gas to clean air may be repeated several times until maximum load is reached.

For load removal the gas flow through the apparatus is interrupted and the heating element 10 is activated. The subsequent burning of the soot may be monitored via a change in resonance frequency and is complete once a stable resonance frequency has been reached. The heating element 10 is then deactivated, clean air is drawn through the measuring cell 1, the resonance frequency assumes its original value before load, and a new measuring cycle may be initiated.

If the resonance frequency is lower after burning than prior to loading, this will indicate deposits (such as mineral fractions of the aerosol particles, dust, etc.) on the oscillating sensor 2, which can only be burnt at extremely high temperatures or cannot be burnt at all. Such deposits usually are rare and will hardly impair the functioning of the apparatus. If the rate of deposits is too high the oscillating sensor 2 must be cleaned manually.

In the variant presented in FIG. 2 a number of measuring cells 1 are connected in parallel, the thermostat devices 5 of which will subject the individual oscillating sensors 2 to different temperatures. On the outlet end the measuring cells 1 are connected to a vacuum pump 8; on the inlet side they are provided with a distributor system 14 admitting the gas sample (arrow 12) or clean air (arrow 11). Switchover is effected by means of the valve 13. An orifice 9 may be provided in the central feeder pipe 15 or at the entrance of each heating chamber 6. The measuring chamber for analysis of the total particle content, which is maintained at a low temperature level, need not be equipped with a thermostat device, and instead of the heating chamber a tubular impactor 16 may be used which is provided with an orifice 9 at the entrance. The other two measuring cells are maintained at temperatures of more than 200° C. and/or more than 500° C.

What is claimed is:

1. Method for determining non-volatile components of aerosol particles in a gas sample, comprising the steps of:
depositing said aerosol particles of said gas sample on a piezoelectric resonator of at least one crystal microbalance, said piezoelectric resonator being temperature stable up to at least 600° C.,
maintaining said piezoelectric resonator of said at least one crystal microbalance at a temperature of more than 200° C. during deposition of said aerosol particles, and
determining a change in at least one oscillation parameter of said piezoelectric resonator as measurement variable of said non-volatile components.

2. Method according to claim 1, wherein said piezoelectric resonator is maintained at a temperature between 250° C. and 350° C.

3. Method according to claim 1, wherein said gas sample is an exhaust gas sample of an internal combustion engine.

4. Method according to claim 1, wherein said gas sample is thermostabilized at a temperature of more than 200° C. prior to deposition on said piezoelectric resonator of said at least one microbalance.

5. Method according to claim 4, wherein said gas sample is thermostabilized at a temperature between 250° C. and 350° C.

6. Method according to claim 1, wherein said piezoelectric resonator is heated to more than 600° C. in order to pyrolytically remove deposited graphitic component of said aerosol particles from said piezoelectric resonator.

7. Method according to claim 6, wherein a change in resonance frequency of said piezoelectric resonator is monitored during pyrolytic removal of said graphitic component for controlling removal status.

8. Method according to claim 6, wherein said piezoelectric resonator is subjected to an oxidizing atmosphere before or during said pyrolytic removal of said graphitic component.

9. Method according to claim 8, wherein said piezoelectric resonator is subjected to clean air.

10. Method according to claim 1, wherein two or more crystal microbalances are used whose piezoelectric resonators are maintained at different temperature levels.

11. Method according to claim 10, wherein for separate measurement of non-volatile graphitic particles and mineral particles of said gas sample, said piezoelectric resonator of a first of said crystal microbalances is maintained at a temperature of more than 200° C., while said piezoelectric resonator of a second of said crystal microbalances is maintained at a temperature of more than 500° C.

12. Method according to claim 11, wherein for measurement of total particle content of said gas sample, said piezoelectric resonator of a third of said crystal microbalances is maintained at a low temperature.

13. Method according to claim 1, wherein deposition of said aerosol particles on a sensitive area of said piezoelectric resonator is effected by low-pressure impaction.

14. Method according to claim 1, wherein at least two oscillator parameters of said piezoelectric resonator are used for determination of said measurement variable, thereby compensating for a non-mass-proportional change in resonance frequency caused by viscoelastic properties of said particles deposited.

15. Method according to claim 14, wherein said oscillator parameters are resonance frequency and attenuation.

16. Apparatus for determining non-volatile components of aerosol particles in a gas sample, having at least one measuring cell provided with gas inlet and containing an piezoelectric resonator of a crystal microbalance subjected to said gas sample, wherein said piezoelectric resonator is temperature stable up to at least 600° C. and is provided with a thermostat device maintaining a temperature of more than 200° C.

17. Apparatus according to claim 16, wherein the temperature is maintained at between 250° C. and 350° C.

18. Apparatus according to claim 16, wherein said thermostat device is provided with a heating chamber placed upstream of said measuring cell, including a nozzle plate for directing said gas sample into said measuring cell.

19. Apparatus according to claim 18, wherein in order to generate a partial vacuum in said measuring cell, an outlet of said measuring cell is connected to a vacuum pump and said heating chamber is provided with an entrance orifice for said gas sample.

20. Apparatus according to claim 18, wherein a plurality of measuring cells are connected in parallel, having thermostat devices to subject said individual piezoelectric resonators to different temperatures.

21. Apparatus according to claim 16, wherein said piezoelectric resonator is provided with a resistance- or radiation-type heating element for heating said oscillating sensor to a temperature of more than 600° C.

22. Apparatus according to claim 16, wherein said piezoelectric resonator is a BAW-resonator made from temperature-stable material of a group consisting of $GaPO_4$, $La_3Ga_5SiO_{14}$, $Sr_3Ga_2Ge_4O_{14}$, $Ca_3Ga_2Ge_4O_{14}$, $Ln_3Nb_{0.5}Ga_{5.5}O_{14}$ and $Ln_3Ta_{0.5}Ga_{5.5}O_{14}$ with Ln=La, Pr, Nd.

* * * * *